United States Patent [19]

Cumming

[11] Patent Number: 4,862,885
[45] Date of Patent: Sep. 5, 1989

[54] INSTRUMENT FOR INSERTING A DEFORMABLE INTRAOCULAR LENS INTO THE EYE

[76] Inventor: J. Stuart Cumming, 1211 W. La Palma Ave., Suite 201, Anaheim, Calif. 92801

[21] Appl. No.: 198,571

[22] Filed: May 25, 1988

[51] Int. Cl.⁴ .............................................. A61B 17/00
[52] U.S. Cl. ................................................. 128/303 R
[58] Field of Search .................... 128/303 R, 321, 325, 128/326, 354

[56] References Cited

U.S. PATENT DOCUMENTS

| | | | |
|---|---|---|---|
| 3,967,625 | 7/1976 | Yoan | 128/326 |
| 4,655,219 | 4/1987 | Petruzzi | 128/321 |
| 4,699,140 | 10/1987 | Holmes et al. | 128/303 R |

Primary Examiner—Michael H. Thaler
Attorney, Agent, or Firm—Keith D. Beecher

[57] ABSTRACT

An instrument for inserting a deformable intraocular lens into the eye, and which is constructed so that the deformable lens is grasped in its undeformed state by two jaws mounted on the end of a shaft which are forced together as the shaft is drawn into a tube, the deformed lens being held in position by the confinement of the jaws by the tube. The tips of the jaws and the deformed lens are inserted through an incision into the eye using the walls of the incision to help compress the jaws and the lens. The lens is then completely inserted into the eye by a plunger mounted coaxially within the shaft and returns to its original undeformed state after it has been so inserted.

6 Claims, 8 Drawing Sheets

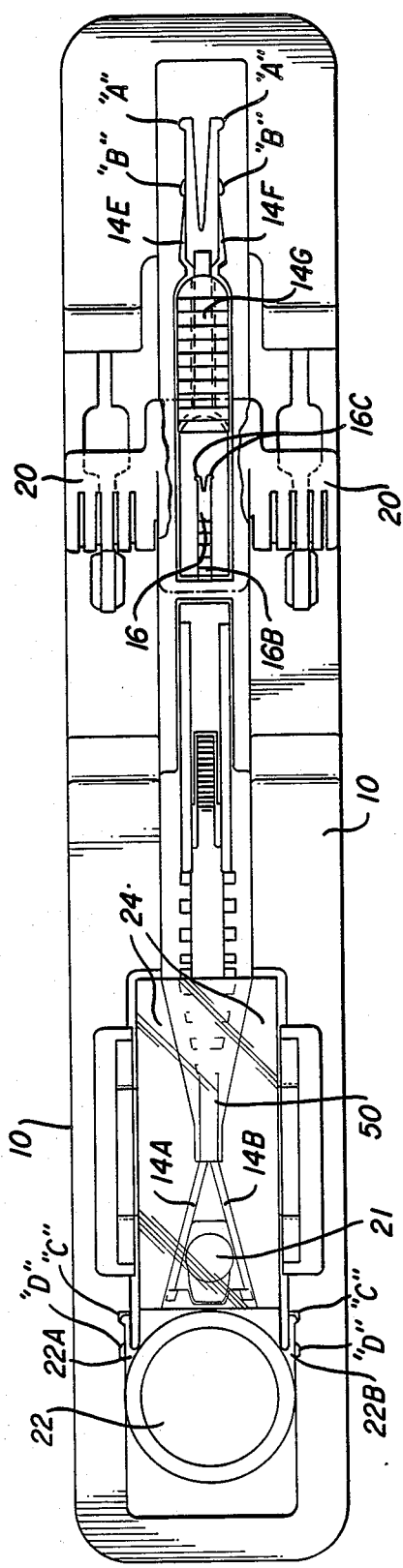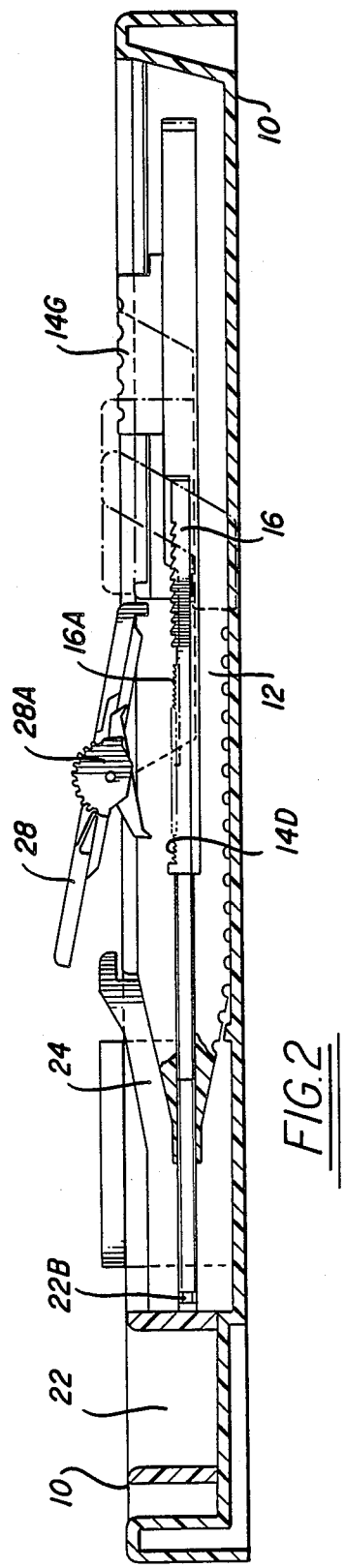

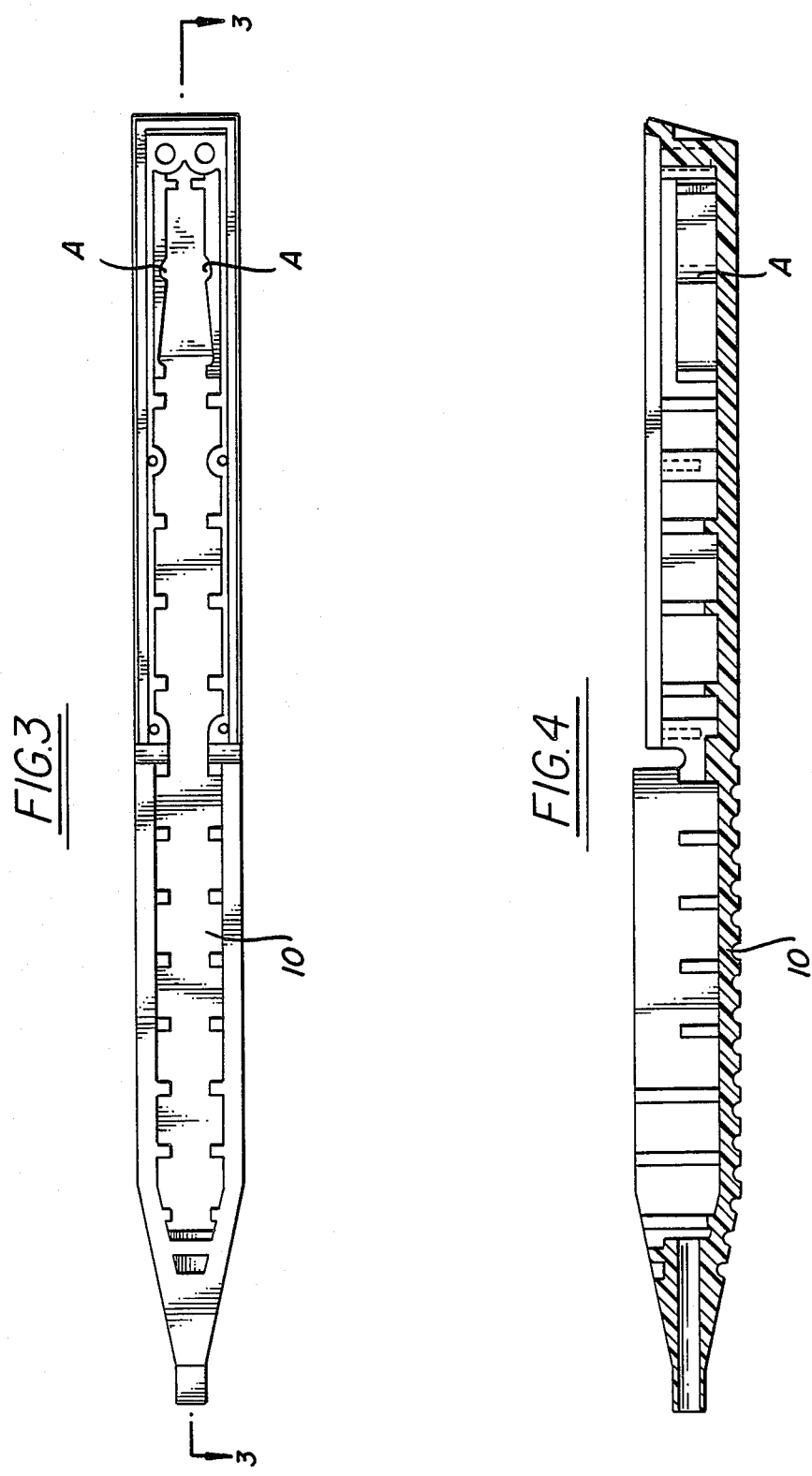

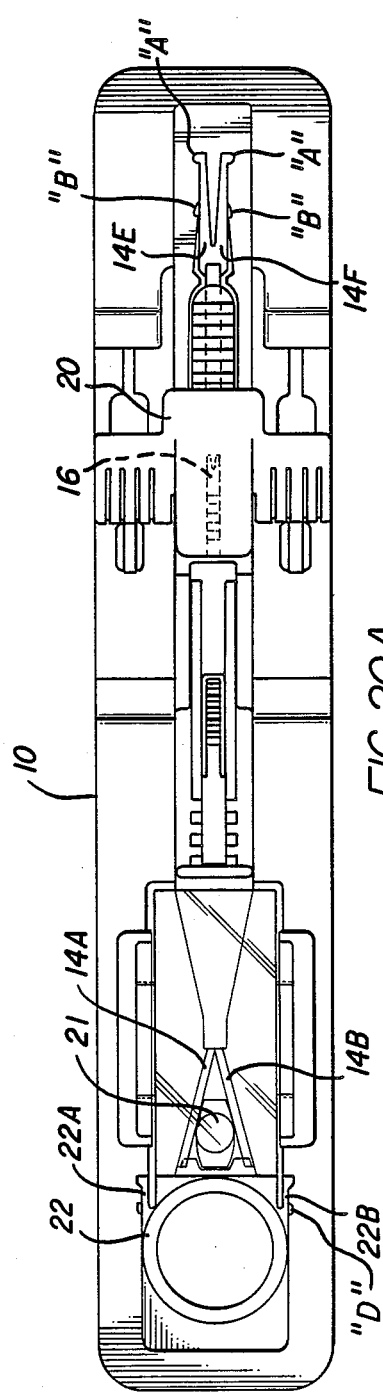
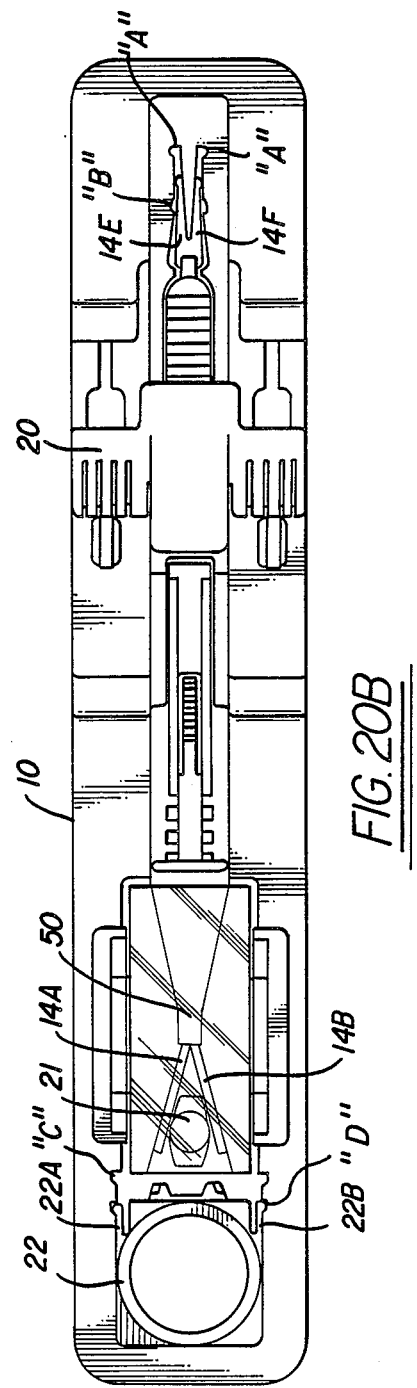

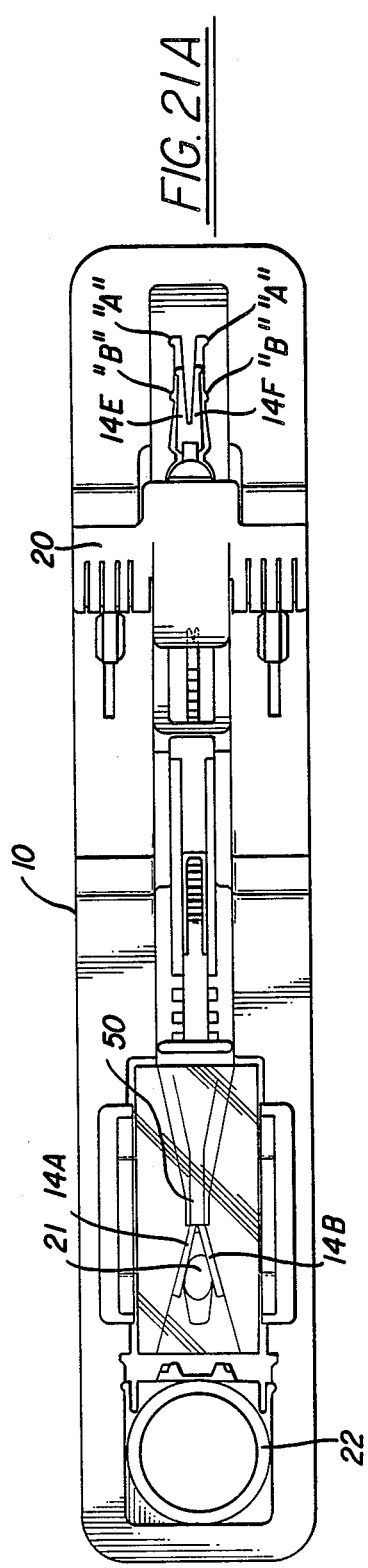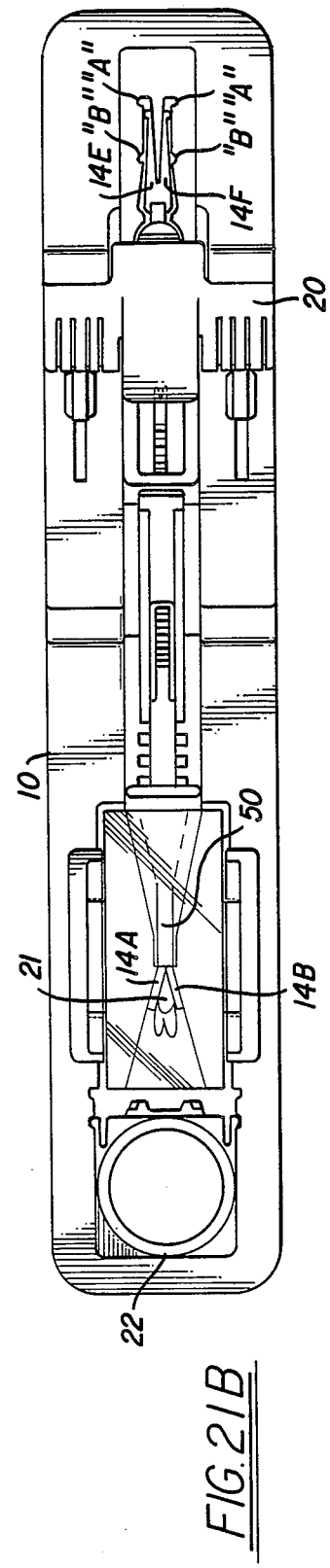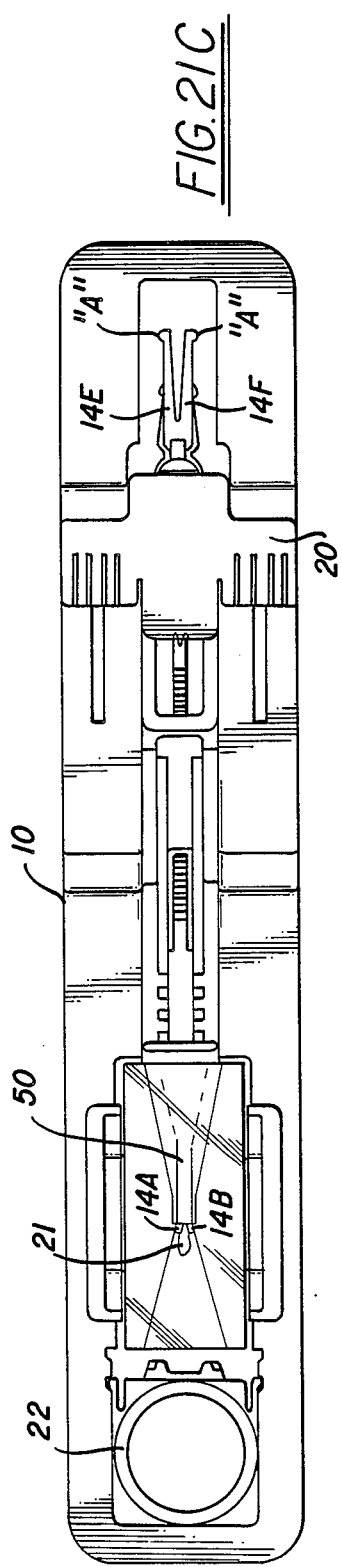

INSTRUMENT FOR INSERTING A DEFORMABLE INTRAOCULAR LENS INTO THE EYE

BACKGROUND OF THE INVENTION

A problem has arisen in the past with respect to intraocular lenses, in that the lens itself has a diameter of the order of 6 millimeters, and the surgeon would prefer to use a smaller incision, because the smaller the incision the more rapid the healing, resulting in more rapid visual and physical rehabilitation and fewer complications. There is also less astigmatism, less discomfort to the patient, a shorter operating time, and thus a reduced cost, when a small incision is used.

A deformable intraocular flexible lens has recently been developed for implantation into the eye. Such a lens is inserted into the eye through a small incision made by the surgeon in the sclera or cornea. A typical insertion method is described, for example, in Mazzocco U.S. Pat. No. 4,573,998.

The deformable intraocular lens referred to above may be deformed to a reduced configuration for insertion into the eye through a relatively small incision. However, the deformable intraocular lens, like other intraocular lenses, includes haptics or loops which serve to secure the lens in position after it has been inserted into the eye. These haptics or loops, as well as the optical zone of the lens, are fragile, and they have a tendency to tear when attempts are made to deform the lens for insertion purposes. If a lens is damaged during insertion the incision must be enlarged to allow the first lens to be removed and a second lens to be inserted. This poses a significant problem in devising a suitable instrument for deforming the lens prior to insertion through the small incision, and one which has no tendency to damage the lens during the deformation process.

Prior art attempts to provide insertion instruments which do not tend to tear off the haptics or loops, or to otherwise damage the lens, have, for the most part, proven to be somewhat unsuccessful.

One such prior art instrument, for example, requires that the lens be loaded by hand during the surgical procedure and inserted into a tube. A reduction nozzle is then screwed onto the tube, and a viscoelastic material is introduced into the other end of the tube by means of a syringe, thereby forcing the lens into and through the reduction nozzle. In this manner, the lens is forced into a smaller and smaller cylinder, under pressure created by the syringe forcing the viscoelastic material against the lens, until the lens is finally released from the nozzle at a relatively high speed into the eye through a 3 to 3.5 millimeter incision. When this prior art instrument is used, the lens frequently tears during the insertion process.

A second prior art instrument is similar to the one described in the preceding paragraph, except that a clam-like hinged tube is employed to help form the lens into a tubular or rolled configuration. However, as the hinged tube is closed, there is a tendency to crimp the lens and damage it.

Both prior art instruments described above require hand loading of the lens. However, any handling of the lens has a tendency to damage it. Moreover, powder from surgical gloves, and other foreign particles, can contaminate the lens. In addition, both prior art instruments described above subject the lens to a substantial pressure as the lens is forced along and squeezed down the tube into the eye.

An objective of the present invention is to provide a simple, inexpensive instrument, which may be disposable, for deforming the lens and thereby reducing its configuration without any need for the surgeon or assistant to handle or touch the lens, and which permits the insertion of the lens into the eye through a small incision, all without any tendency to tear off the haptics or loops or otherwise to damage or contaminate the lens.

The present invention is generally similar in some respects to the instrument described in Hauser U.S. Pat. No. 4,763,650 which issued Aug. 16, 1988.

BRIEF DESCRIPTION OF THE DRAWINGS

FIG. 1 is a top plan view of one embodiment of the present invention supported in a tray, and with certain components removed for purposes of clarity;

FIG. 2 is a side elevational view of the instrument of FIG. 1 with a side wall of the housing of the instrument removed, again for purposes of clarity;

FIG. 3 is a top plan view of the housing of the instrument of FIGS. 1 and 2;

FIG. 4 is a longitudinal section of the housing of FIG. 3, taken along the line 3—3;

FIGS. 20A and 20B are schematic representations showing the manner in which certain jaws of the instrument of FIGS. 7 and 8 are originally held apart, and how the jaws are released to engage the deformable lens which is to be inserted by the instrument of the invention; and FIGS. 21A, 21B and 21C are schematic representations showing the manner in which the instrument of the invention is loaded.

DETAILED DESCRIPTION OF THE ILLUSTRATED EMBODIMENT

In the practice of the present invention, the lens to be inserted into the eye of a patient is delivered to the surgeon in a sterile package. Also included in the package is a disposable insertion instrument constructed in accordance with the teachings of the present invention, and other elements required for loading the lens into the instrument. The instrument is effective in deforming the lens from a flat configuration into a compressed shape, as the lens is loaded into the instrument, to enable the lens to be inserted by the instrument into the eye through a relatively small incision.

The jaws of the instrument of the invention are required to reduce the size of the lens from 6 millimeters to 4 millimeters, or less, for example, during the loading operation, so that the lens may be inserted into the eye through a relatively small incision. During the insertion operation, the forward ends of the jaws must be inserted through the incision along with the deformed lens. Thus, a criteria for the insertion portion of the instrument is that it must be very thin, in order to enable it and the deformed lens to fit into the small incision. This precludes the use of tweezer-like instruments for the insertion process, because any tweezer jaws made to the required thinness would have no squeezing force.

One embodiment of the invention is shown in FIGS. 1–20A, 20B, 21A, 21B and 21C.

Figure 5:
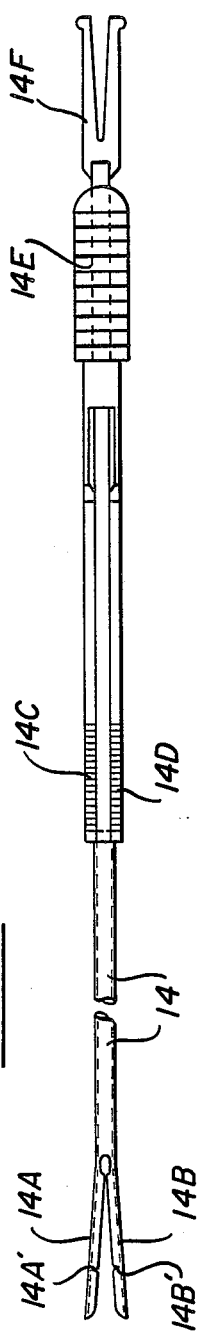
FIG. 5 is a top plan view of a jaw shaft which is included in the instrument of FIGS. 1 and 2.
Figure 6:
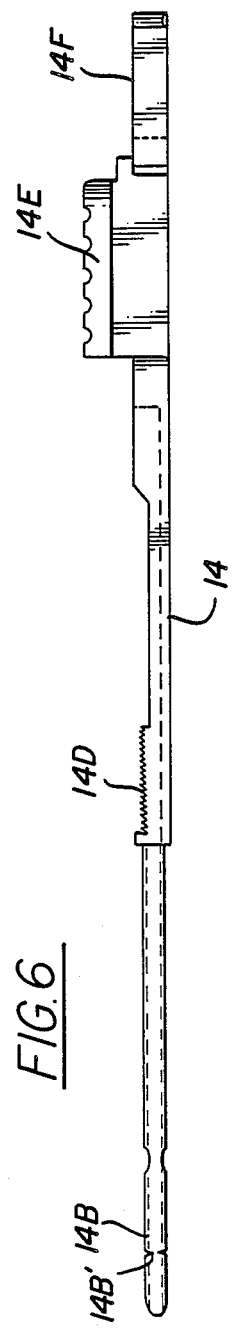
FIG. 6 is a side elevation of the jaw shaft of FIG. 5.

As shown in FIGS. 1 and 2, the instrument of the invention is normally held in a tray 10. The instrument includes a housing 12, and a jaw shaft 14 is slidably supported in the housing. A pair of jaws 14A and 14B are affixed to the forward end of the jaw shaft. The jaws have notches 14'A and 14'B which form hinges. A plunger 16 is also slidably supported on housing 12, and the plunger extends into the jaw shaft 14 in coaxial relationship with the jaw shaft. The plunger 16 has a first ratchet 16A and a second ratchet 16B. The jaw shaft 14 has a pair of ratchets 14C and 14D spaced from one another, and the ratchet 16A of the plunger is received between the ratchets 14C and 14D. Details of the jaw shaft are shown in FIGS. 5 and 6. The jaw shaft 14 has further jaws 14E and 14F on its right-hand end in FIGS. 1, 2, 5 and 6.

Figure 7:
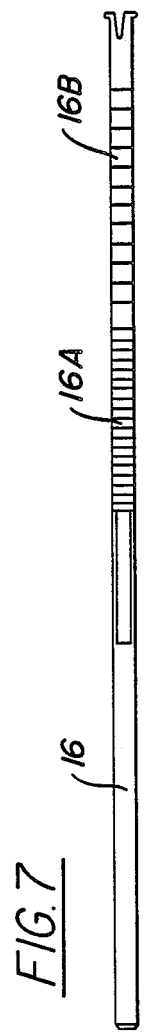
FIG. 7 is a top plan view of a plunger which is included in the instrument of FIGS. 1 and 2.
Figure 8:
FIG. 8 is a side view of the plunger of FIG. 7.
Figure 18:
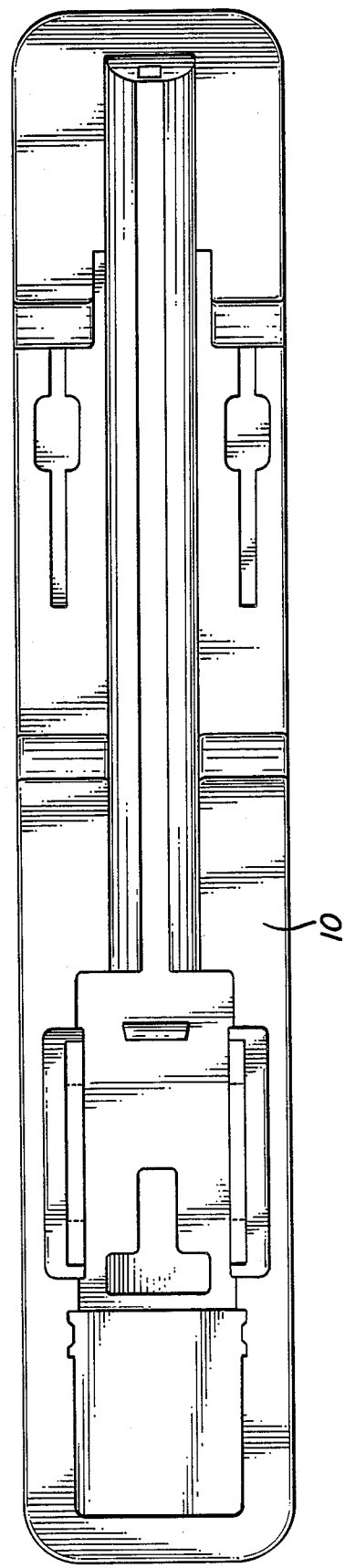
FIG. 18 is a top plan view of a tray in which the instrument of FIGS. 1 and 2 is supported.
Figure 19:
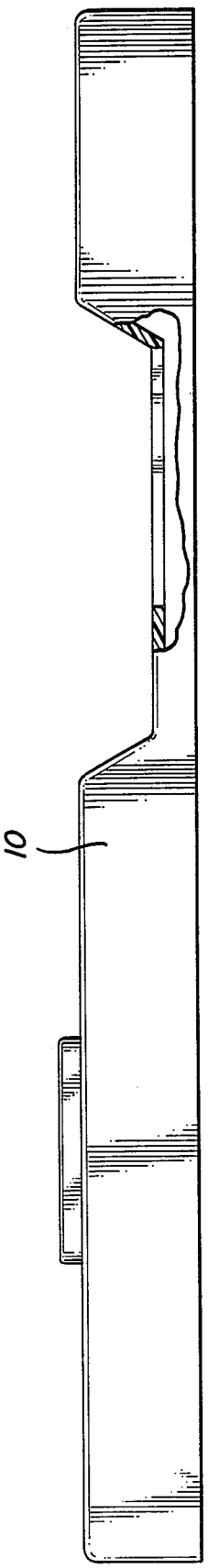
FIG. 19 is a side elevation of the tray of FIG. 18, partly in section.

Details of plunger 16 are shown in FIGS. 7 and 8. Details of housing 10 are shown in FIGS. 3 and 4. Details of tray 10 are shown in FIGS. 18 and 19.

Figure 9:
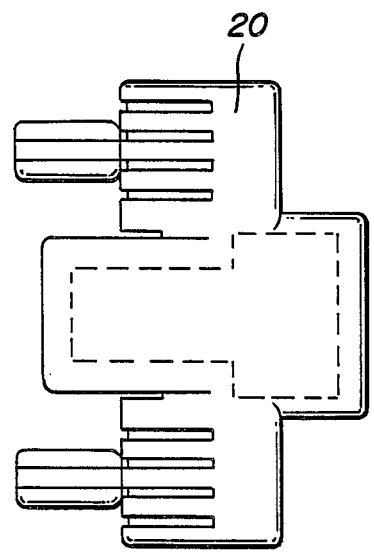
FIG. 9 is a top plan view of a finger pull element which is included in the instrument of FIGS. 1 and 2.
Figure 10:
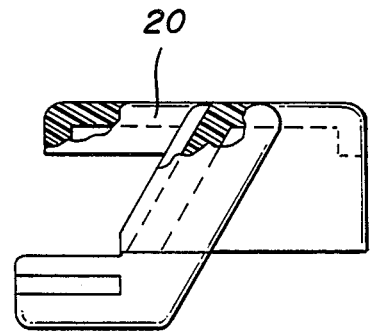
FIG. 10 is a side elevation, partly in section, of the finger pull element of FIG. 9.

Plunger 16 extends into a finger pull member 20, and is frictionally held in the finger pull by split ends 16C, as shown in FIG. 1. Jaw shaft 14 extends through the finger pull and it includes a rear member 14G which engages the rear end of the finger pull. Details of the finger pull are shown in FIGS. 9 and 10. As the jaw shaft 14 is pulled to the right in FIGS. 1 and 2 by the finger pull 20, the ends of ears 14E, 14F, move from engagement with detents A into engagement with detents B.

Figure 11:
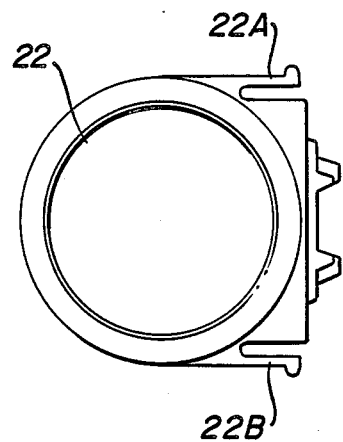
FIG. 11 is a top plan view of a jaw holder ring which is included in the instrument of FIGS. 1 and 2.
Figure 12:
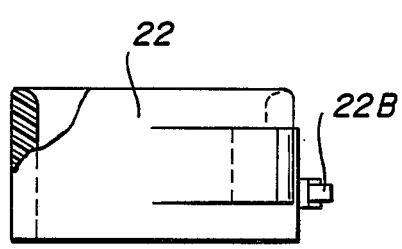
FIG. 12 is a side elevation, partly in section, of the jaw holder ring of FIG. 11.

A lens 21 is positioned between the jaws 14A, as shown in FIG. 1, with the jaws being held out of contact with the lens by a jaw holder ring member 22, when the arms 22A and 22B of the ring member engage detents C. However, when the ring member is pulled to the left in FIG. 1 until its arms 22A, 22B engage detents D, the jaws are released and move against the sides of lens 21. Details of the jaw holder ring are shown in FIGS. 11 and 12.

Figure 14:
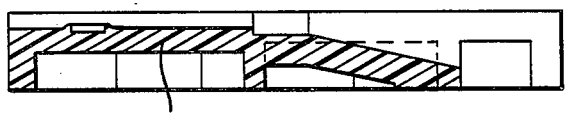
FIG. 14 is a longitudinal section of the ramp of FIG. 13 taken along the line 14—14 of FIG. 13.
Figure 15:
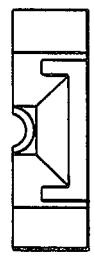
FIG. 15 is an end view of the ramp of FIG. 13 taken from the right in FIG. 13.
Figure 13:
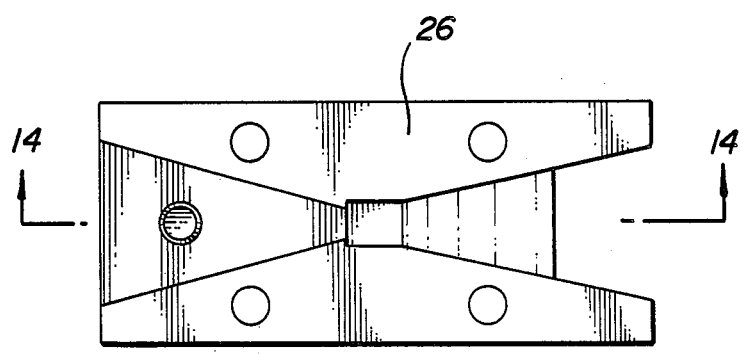
FIG. 13 is a top plan view of a lower ramp which is included in the instrument of FIGS. 1 and 2.
Figure 17:
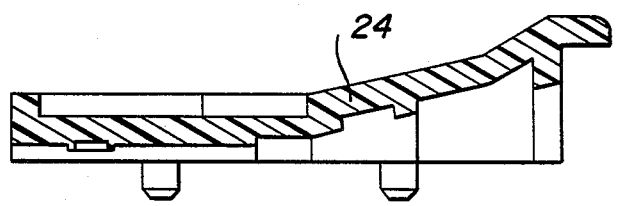
FIG. 17 is a longitudinal section of the ramp of FIG. 16 taken along the line 17—17.
Figure 16:
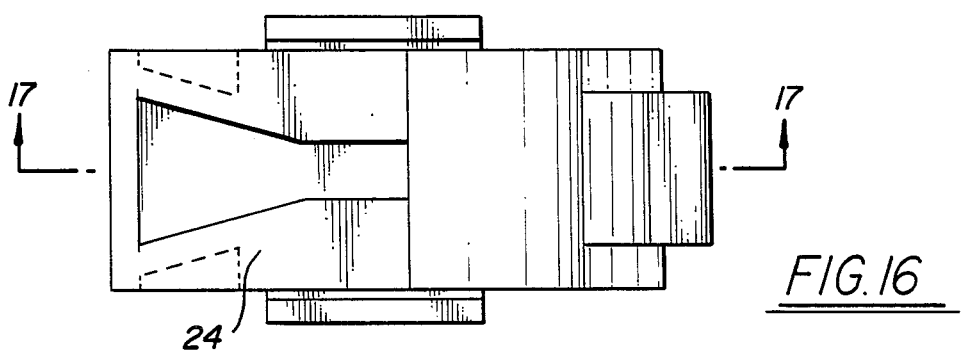
FIG. 16 is a top plan view of an upper ramp included in the instrument of FIGS. 1 and 2.

The assembly includes an upper ramp 24, and a lower ramp 26. Details of the upper ramp are shown in FIGS. 16 and 17, and details of the lower ramp are shown in FIGS. 13 and 14. The assembly also includes an inserter 28 which is shown in FIG. 2. The inserter includes a double-acting pawl 28A which, when set to one position engages the ratchets 14C, 14D of the jaw shaft 14 and ratchet 16A of plunger 16, incrementally to move the jaw shaft and the plunger to the left in FIG. 2. When set to its second position, the pawl 28A of inserter 28 engages the ratchet 16B of plunger 16 to move the plunger to the right in FIG. 2.

FIGS. 20A and 20B are schematic diagrams representing the initial steps in activating the instrument of the invention. The representation of FIG. 20A is similar to that of FIG. 1, and represents the rest or packaged position of the lens and instrument in tray 10, as the tray is received from the manufacturer. In that position, the arms 22A, 22B of the jaw holder ring member 22 are held in detents C, and the ring member is locked in position to hold the jaws 14A and 14B of the jaw shaft 14 out of contact with lens 21. The jaw shaft 14 is now in its forward position, with its ears 14E and 14F engaging detents B. The finger pull 20 is now in its forward position, and plunger 16 is in its rear position with its right-hand end contacting the finger pull and held frictionally in the finger pull.

As an initial operation, the protective wrapping is removed from the assembly of FIG. 20A, and ring 22 is pulled to the left in FIG. 20B by placing a finger in the ring 22, and a thumb at the end of tray 10, so that the ring is pulled to the position of FIG. 20B with its arms 22A and 22B engaging detents D.

The finger pull 20 is then moved towards the right in FIG. 20B by placing the thumbs on the right-hand end of tray 10 and the index fingers on the front surface of the finger pull, and then exerting a squeezing motion. This pulls the jaws 14A and 14B into a tube 50 at the front of the instrument, as the ears move along the inner surfaces of the upper ramp 24 and lower ramp 26. At this time, the ears 14E and 14F at the other end of the jaw shaft 14 move from detents B towards detents A. The aforesaid action of the jaws 14A and 14B, as they are drawn into tube 50 compresses the lens as the jaws move along the ramp walls.

Subsequent movements are shown in FIGS. 21A and 21B, with the lens 21 being compressed more and more, as the jaws 14A, 14B are pulled into the tube 50. This action, as mentioned above, is caused by squeezing the finger pull 20 towards the rear end of the tray, and this motion pulls the jaw shaft 14 into the tube 50 moving the ears 14A, 14B along the ramps compressing the jaws and the lens. As shown in FIGS. 21A and 21B, the ears 14E and 14F of the jaw shaft move from detents B towards detents A, and they are pressed together during the motion. The ears 14E and 14F finally come to rest in detents A, as shown in FIG. 21C.

When the instrument reaches the position of FIG. 21C, the jaws 14A and 14B are almost completely pulled into the tube 50, with the tail end of the lens 21 protruding from the end of the tube, as shown.

The finger pull 20 is now removed, and inserter 28 is placed in the position shown in FIG. 2, and its pawl 28A is turned counterclockwise to engage both ratchets 14C, 14D of the jaw shaft 14 and ratchet 16A of plunger 16. Then, operation of the inserter causes the jaw shaft and the plunger to move together to the left in FIG. 2. Subsequently, the pawl disengages from the jaw ratchet and advances the plunger 16 only from that point on. This occurs when the ends of the jaws have entered the incision in the eye, and the subsequent motion of the plunger pushes the lens 21 into the eye. The jaws then open on hinges 14'A and 14'B. When that operation is completed, pawl 28A is reversed, and engages ratchet 16 of the plunger to retract the plunger from the lens, and to move the plunger back to its original position of FIGS. 1 and 2.

An important aspect of the instrument of the invention, as described above, is that it permits the insertion of the lens into the eye of the patient without the lens having to move through a confining tube as it is inserted into the eye.

It will be appreciated that while a particular embodiment of the invention has been shown and described, modifications may be made. It is intended in the claims to cover all modifications which come within the true spirit and scope of the invention.

We claim:

1. An instrument for inserting a deformable intraocular lens through a small incision into the eye, the incision having a reduced diameter with respect to the diameter of the lens, and the lens being inserted through the incision in a deformed configuration, said instrument including: a tube; a shaft positioned coaxially within said tube for axial movement with respect to said tube; a plunger coaxially positioned within said shaft and axially movable with respect to said shaft; and means for initially moving said shaft and said plunger together with respect to said tube and then to move said plunger independently of said shaft to cause the end of the plunger to engage the lens and move the lens into the eye, and which includes clamping means attached to the distal end of said shaft in axial relationship therewith, said clamping means being moved axially in and out of said tube upon reciprocal axial movement of said shaft with respect to said tube and said clamping means serving to receive an undeformed deformable intraocular lens while out of said tube to be deformed thereby as said clamping means is moved into said tube by said shaft.

2. The instrument defined in claim 1, in which said clamping means comprises a pair of normally open jaws which are closed against one another as said clamping means is moved into said tubes by said shaft.

3. The instrument defined in claim 2, in which said jaws are detachable from said shaft.

4. The instrument defined in claim 2, in which said jaws normally have a spread-apart configuration when positioned out of the confines of said tube, and in which said jaws return to said spread-apart configuration when they are moved out of the confines of said tube.

5. The instrument defined in claim 2, in which at least one of said jaws has an intermediate hinge formed therein.

6. The instrument defined in claim 1, in which said shaft and said plunger have ratchet teeth formed thereon, and in which said moving means comprises a pawl engaging said ratchet teeth, and in which said pawl engages said teeth to move said shaft and said plunger together a predetermined distance, and then to move said plunger independently of said shaft to cause the end of the plunger to engage the lens and move the lens into the eye.

* * * * *